(12) United States Patent
Schultz

(10) Patent No.: US 6,437,159 B1
(45) Date of Patent: *Aug. 20, 2002

(54) FLUORINATED ALKANOIC ACID PURIFICATION PROCESS

(75) Inventor: James Arnold Schultz, Swedesboro, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/682,172

(22) Filed: Jul. 31, 2001

Related U.S. Application Data

(63) Continuation-in-part of application No. 09/644,165, filed on Aug. 23, 2000, now Pat. No. 6,281,374.

(51) Int. Cl.$^7$ .................................. C11B 8/00
(52) U.S. Cl. ................ 554/188; 554/226; 554/187; 562/605
(58) Field of Search ................ 504/187, 188; 562/226, 605

(56) References Cited

U.S. PATENT DOCUMENTS

| | | |
|---|---|---|
| 3,833,626 A | 9/1974 | Ferse et al. |
| 4,282,162 A | 8/1981 | Kuhls |
| 4,609,497 A | 9/1986 | Cope |
| 5,312,935 A | 5/1994 | Mayer et al. |
| 5,442,097 A | 8/1995 | Obermeier et al. |
| 5,591,877 A | 1/1997 | Obermeier |
| 6,281,374 B1 * | 8/2001 | Schultz ................ 554/226 |

FOREIGN PATENT DOCUMENTS

| | | |
|---|---|---|
| JP | 01117840 | 9/1993 |
| JP | 96231462 | 9/1996 |

* cited by examiner

*Primary Examiner*—Deborah D Carr

(57) ABSTRACT

A process that can be used for isolating a fluorinated alkanoic acid from an aqueous solution also containing inorganic fluorides is provided. This process comprises (A) acidifying an aqueous solution comprising an ammonium or metal salt of a fluorinated alkanoic acid to produce an acidified solution, (B) heating the acidified solution to produce an organic layer and an aqueous layer, (C) separating and recovering the organic layer from the aqueous layer, (D) optionally washing the organic layer with an acid solution, (E) optionally isolating the fluorinated alkanoic acid, and (F) further optionally converting the fluorinated alkanoic acid to its ammonium or alkali metal salt.

17 Claims, No Drawings

FLUORINATED ALKANOIC ACID PURIFICATION PROCESS

CROSS REFERENCE TO RELATED APPLICATION

This application is a continuation-in-part of application Ser. No. 09/644,165 filed Aug. 23, 2000 now U.S. Pat. No. 6,281,374.

BACKGROUND OF INVENTION

This invention relates to a process for the purification of fluorinated alkanoic acids such as, for example, perfluorooctanoic acid, from aqueous solutions of their salts.

The ammonium or alkali metal salts of fluorinated alkanoic acids are generally used in the aqueous emulsion polymerization of fluorinated olefin monomers such as tetrafluoroethylene, chlorotrifluoroethylene or vinylidene fluoride because of their high surface activity and low rate of telogen formation. In the course of these polymerizations, some of the fluorinated olefins hydrolyze to produce fluoride ions. After polymerization is complete and the resulting fluoropolymer is isolated, the fluorinated alkanoic acid ammonium or alkali metal salt is present in a dilute aqueous solution, along with ionic fluorides and other impurities. It is highly desirable to recover these fluorinated alkanoic acids and their salts for reuse, both because of their high cost and the need to minimize pollution problems. For such reuse, any impurities in the recovered compounds that may inhibit or change the course of the subsequent polymerization must be removed. Of particular use in such applications are the ammonium or alkali metal salts of fluorinated alkanoic acids, such as, for example, perfluorooctanoic acid (PFOA).

A known method of purification is by acidifying a fluorinated alkanoic ammonium or alkali metal salt solution by adding sulfuric acid until a pH of 1 to 2 is obtained, and subjecting the acidified solution to steam distillation. This is an energy-inefficient process, and yields a dilute solution of about 10–16 wt % fluorinated alkanoic acid. This must be neutralized with ammonia or alkali metal and concentrated for reuse by a means such as reverse osmosis. In an additional difficulty, the fluorides in the solution can co-distill during the steam distillation and corrode the distillation equipment.

U.S. Pat. No. 4,609,497 discloses a process for the recovery of ammonium or alkali metal salt of PFOA from a solution containing a selected nonionic polyether by extracting the ammonium salt with an organic liquid, decanting the organic layer containing the PFOA, contacting it with alumina to adsorb the PFOA, contacting the alumina with ammonium hydroxide to remove the PFOA, acidifying and decanting the resulting solution, steam distilling the organic phase in the presence of an acid and an oxidizing agent, and neutralizing the PFOA with ammonium hydroxide. This process is cumbersome to carry out, and requires the addition and removal of an organic extractant and an alumina adsorbent.

U.S. Pat. No. 4,282,162 discloses a process wherein, after a fluorinated carboxylic acid has been recovered from an aqueous solution by adsorption on a basic ion exchanger; it is eluted using a mixture of a mineral acid and an organic solvent. The eluate is then decanted, the lower organic layer neutralized and acidified, and the precipitated fluorinated carboxylic acid filtered. The fluorinated carboxylic acid obtained by this process is not of polymerization grade. U.S. Pat. No. 5,312,935 discloses a process for purifying such acid by oxidizing it in a solution containing less than 9% by weight of water. This process requires special ion exchange equipment, frequent replacement of the ion exchange resin, the addition and removal of an organic solvent, and a further purification step.

U.S. Pat. Nos. 5,442,097 and 5,591,877 disclose a process for recovery of fluorinated carboxylic emulsifiers from an aqueous solution containing its salt by acidification of the salt, reacting the acid with an alcohol to form the ester, distilling the resulting ester mixture, and decanting the ester layer. The resulting ester may be reacted with aqueous ammonia to form the corresponding ammonium salt. This process requires introduction of an organic reactant, which must be recovered, and requires carrying out additional esterification and de-esterification reactions.

The above processes are complicated and expensive to carry out, requiring multiple conversion steps in which the fluorinated alkanoic compound is either transferred to other media, such as an organic solvent or adsorbing solid, or converted to an organic ester, followed by transfer or conversion back to the fluorinated alkanoic compound. There is a need to develop a simpler process in which the fluorinated alkanoic acid can be isolated by an efficient means, and without such transfers or conversions. An advantage of the invention is that the invention process does not require transferring the fluorinated alkanoic acid to an organic solvent or an adsorbent, or its conversion to an organic ester. Another advantage of the invention is it does not require concentration of the purified ammonium or alkali metal salt solution with reverse osmosis, and it minimizes the content of corrosion-causing fluorides.

SUMMARY OF INVENTION

A process that can be used for isolating a fluorinated alkanoic acid from an aqueous solution also containing inorganic fluorides is provided. This process comprises (A) acidifying an aqueous solution comprising an ammonium or alkali metal salt of a fluorinated alkanoic acid to produce an acidified solution, (B) heating the acidified solution to produce an organic layer and an aqueous layer in which the organic layer comprises the fluorinated alkanoic acid, (C) separating and recovering the organic layer from the aqueous layer, (D) optionally washing the organic layer with an acid solution, (E) optionally isolating the fluorinated alkanoic acid, and (F) further optionally converting the fluorinated alkanoic acid to its ammonium or alkali metal salt.

DETAILED DESCRIPTION

The present invention can be used to isolate any fluorinated alkanoic acid. The fluorinated alkanoic acid can have the general formula of $X\text{-}R_f\text{—COOH}$ in which X is hydrogen, fluorine, chlorine, or combinations thereof and $R_f$ is a fluorinated group that can be saturated or unsaturated, linear or branched such as methyl-branched alkylene group having 5 to 12, preferably 5 to 10 carbon atoms per group. Generally the fluorinated alkanoic acid can contain some inorganic fluorides, from about 5 to about 1200, more typically about 10 to about 1000 mg/kg of the fluorinated alkanoic acid (ppm). The fluorinated alkanoic acid can be present as an aqueous solution of a metal or, preferably, ammonium salt.

Examples of such fluorinated alkanoic acids include, but are not limited to, perchlorofluoroalkanoic acids and perfluoroalkanoic acids. One such perfluoroalkanoic acid is perfluorooctanoic acid, also called perfluorocaprylic acid.

Optionally, the aqueous solution can be, before or after step (A), treated with an amount of a soluble aluminum salt. Preferably the amount of aluminum salt is at least equivalent to the inorganic fluoride content present in the aqueous solution. The treatment can be carried out for an effective period of time such that the inorganic fluorides are reacted to form mixed aluminum fluorides. The mixed aluminum fluorides can then be substantially removed in the separation step (C). Preferably this treatment is done before step (A). Also preferably the aluminum salt is soluble over the pH range of the process, and contains the same counter-ion as the acid to be used in step (A). For example, if the acid used in step (A) is sulfuric acid, the preferred aluminum salt is aluminum sulfate. The temperature of treatment can be any convenient temperature. This optional step is particularly preferred if the initial aqueous solution is high in fluorides. Using this procedure, the fluoride content of the fluorinated alkanoic acid and the amount of distillation residue can be reduced to an acceptable level, which means that the residue can be easily removed, for the recovery process.

Any acid that does not interfere or react with the fluorinated alkanoic acid can be used in step (A). The preferred acid is a mineral acid to react with the fluoroalkanoate and form the free fluorinated alkanoic acid, which is only slightly soluble in the mineral acid under these conditions. Examples of preferred acids are those well-known mineral acids. Also preferred is that the mineral acid contains less than about 50 volume % water because above 50 volume % can increase the amount of water present in the resulting mixture and therefore the solubility losses for the fluorinated alkanoic acid. If the final purification is distillation, the preferred acid is a relatively nonvolatile acid that does not co-distill during distillation, such as sulfuric acid, phosphoric acid, or nitric acid. The preferred acid is sulfuric acid because of its low volatility. If the final purification step is by crystallization or other means, any mineral acid is satisfactory.

The amount of acid is preferably an amount sufficient or effective to neutralize the ammonium or metal content of the fluorinated alkanoic acid salt and to provide an acid environment sufficient to minimize the solubility of the resulting fluorinated alkanoic acid. Generally the amount can be determined by the pH of the acidified aqueous solution, which can be any pH that can facilitate the isolation or separation of the fluorinated alkanoic acid. The pH can be as low as about 2 or lower. Excess acid, however, can be difficult to remove completely in later steps and is preferably avoided. For example, with sulfuric acid, the preferred amount is about 1 to about 4, preferably about 1 to about 3, and most preferably about 1.3 times the theoretical amount required for neutralizing the ammonium or metal ions, based on only one proton of the sulfuric acid being used.

In step (B), the acidified solution can be heated to a temperature and for a period of time sufficient or effective to produce an organic (lower) layer and an aqueous (upper) layer. Generally the temperature is preferably above the melting point of the wet fluorinated alkanoic acid. The wet melting point is appreciably lower than that of the dry or anhydrous fluorinated alkanoic acid because of the solubilizing effect of the contained water. For example, it was found the water content for perfluorooctanoic acid to be about 12–15% at this point in the process, and that it is a liquid at temperatures above 35–40° C. in the process even though pure perfluorooctanoic acid has a melting point of 55–56° C. The separation temperature may be between about 35 and 60° C. A separation temperature of 45 to 50° C. is preferred. At temperatures above about 60° C., the solubility losses of perfluorooctanoic acid in the aqueous layer may become excessive. For other fluorinated alkanoic acids, the separation temperature is preferably only slightly above the melting point for the wet fluorinated alkanoic acid, and below the point where excessive solubility losses occur.

Wishing not to be bound by theory, if the heating is carried out at temperatures below the melting point of the wet fluorinated alkanoic acid, the fluorinated alkanoic acid may be initially present as small particles dispersed throughout the total liquid, making isolation difficult. However, upon raising the temperature above the fluorinated alkanoic acid's melting point, these particles soon coalesce into a separate liquid phase. This phase can then be easily separated from the aqueous phase by simple decantation, since the phases form a relatively clean separation with a minimum interfacial layer.

Thereafter, in step (C) the aqueous upper layer is separated from the organic lower layer. Any means known to one skilled in the art can be used in the separation. Presently decantation is preferred for it is simple and easy to use. Separation removes most of the water and with it a major portion of the water-soluble impurities.

The recovered organic layer can be washed with a diluted acid solution. The acid can be the same as that used in step (A). The amount of the diluted acid is preferably effective to remove most of the dissolved acid. It is preferred that the diluted acid contains less than about 10 volume % acid to produce a purified fluorinated alkanoic acid. For example, about 5 volume % sulfuric acid can be satisfactory for the diluted or weak acid wash. One or more acid washes can be carried out if desired to minimize distillation residue. Excessive washing such as, for example, more than 3 washes, is preferably avoided because of solubility losses for the fluorinated alkanoic acid. The wash can be conducted at any temperature, preferably at about 10 to about 60° C. more preferably about 35 to about 60° C., and, most preferably 35 to 50° C. A water wash is not recommended since it may create emulsion problems due to ionization of the fluorinated alkanoic acid.

The purified fluorinated alkanoic acid can be recovered from the washed organic layer by any means known to one skilled in the art such as, for example, distillation and crystallization. Distillation is generally preferred. For example, in a batch distillation, the first material overhead is generally the fraction that co-distills with the small amount of dissolved water by a steam distillation effect. This fraction can also contain most of any fluorides that remain, in the form of the volatile hydrogen fluoride. This fraction can be combined with the main product fractions or recycled back to the start of the purification process, depending on its amount and quality. After the dissolved water is removed, the temperature of the distillation generally rises to that of the boiling point of the fluorinated alkanoic acid, which can be then readily vacuum distilled to a receiving vessel. For fluorinated alkanoic acids, which are waxy solids at ambient temperature, such as perfluorooctanoic acid, it is preferred to keep tempered water on the condenser to keep them from freezing out during distillation and plugging the condenser. If desired, the molten product can be mixed with water to depress its freezing point, reacted with ammonia to a pH about 5.5, and the solids adjusted to a standard level for reuse as an emulsifier. The amount of distillation residue remaining is relatively small, depending on the efficiency of washing. It can be removed by refluxing with a sodium hydroxide solution.

The resulting purified fluorinated alkanoic acid from step (E) can readily be converted to the ammonium or alkali metal salt and reused in a polymerization reaction. For convenience, it can be neutralized to a pH of about 5.5 and standardized with water to an appropriate concentration of ammonium or alkali metal fluorinated alkanoate for subsequent use.

The process of the invention can be used for substantially increasing the concentration of a fluorinated alkanoic acid alkali metal or ammonium salt from a dilute aqueous solution of the fluorinated alkanoic acid ammonium or alkali metal salt as low as about 10 weight %. At the same time, the fluorinated alkanoic acid ammonium salt can be separated from nearly all impurities such as low molecular weight organic fluorides and inorganic fluorides, making it suitable for reuse in polymerization reactions.

The process can be run as a batch or continuous operation. Steps prior to distillation could be carried out in a single contacting device.

The efficacy of this simple process is surprising, since previously referenced U.S. Pat. Nos. 5,442,097 and 5,591,877 both disclose that, if the original aqueous solution of the salt is acidified with sulfuric acid, and attempts are made to distill the resulting fluorinated carboxylic acids, they fail since these acids form crystallizing hydrates which can block up the distillation equipment. Moreover, distillation residues are produced in this case which still contain considerable amounts of fluorine, the disposal of which is very complex. The inventive process avoids these difficulties.

Preferably the fluorinated alkanoic acid recovered in the invention process is a perfluorinated alkanoic acid, and still more preferably is perfluorooctanoic acid.

The following examples are intended to illustrate the inventive process, but should not be interpreted as limiting the scope of the invention in anyway.

EXAMPLE 1

To a 1 liter-sample of 20 wt % ammonium PFOA having 780 parts per million by weight (ppm) of fluoride ion was added 200 ml of saturated aluminum sulfate (($Al_2(SO_4)_3$) solution. The mixture was heated to 50° C. and stirred for two hours. A white precipitate was present. Then 100 g of concentrated sulfuric acid was added slowly, with a 10° C. heat rise. The mixture was stirred at 50° C. for one hour, and the phases were partially separated to simulate a single reactor dip tube method of separation. That is, about 80% of the upper aqueous phase was withdrawn, and the bottom organic phase was washed with 300 ml of 5 volume % sulfuric acid. After 5 minutes, the entire phase was separated and the organic phase re-washed with 5 volume % sulfuric acid. The organic phase, containing the PFOA, weighed 363 g. This was then distilled at atmospheric pressure. The first cut (the steam distillation cut) was taken with a still-pot temperature of 106° C. and a head temperature of 102° C., and weighed 103 g. The fluoride content was only 17 ppm. The second cut was taken at atmospheric pressure with a still-pot temperature of 145° C. and a head temperature of 142° C., and weighed 48 g. This was considered transition material. The third cut was taken at a vacuum of 27 inches (68.6 cm) of mercury, a still-pot temperature of 145° C., and a head temperature of 142° C. One hundred ninety (190) g of PFOA product was recovered. The fluoride content was 7 ppm. The still-pot residue weighed only 3 g. It was removed by refluxing 50 ml of 6 weight % NaOH solution for three hours and a second wash of 14 weight % NaOH refluxed for two hours.

By comparison, a similar run without the dilute acid washes, i.e., using only the initial phase cut separation step, gave a still-pot residue weighing 44 g.

EXAMPLE 2

A test was carried out on PFOA that had been processed to remove fluorides by passing through a packed column containing solid aluminum oxide granules. An 8,420 g solution of 20 weight % PFOA ammonium salt containing 17 ppm of fluorides was treated with 768 gm of concentrated sulfuric acid. Decantation and distillation were carried out as in Example 1, but without the treatment with aluminum sulfate. After decantation, the aqueous layer weighed 6507 g and contained 77% of the original fluorides. The organic layer weighed 2681 g. After distillation, the steam distillation cut weighed 495 g and contained 4 weight % of PFOA and 81 ppm fluorides. The transition cut weighed 270 gm and contained 26 wt % PFOA and 33 ppm fluorides. The first vacuum distillation cut weighed 164 g and contained 70 wt % PFOA and only 7 ppm fluorides, and the second cut weighed 1240 g of pure PFOA. The pot residue was 116 g.

This example shows that the fluoride content of the vacuum distillation cuts was excellent using the inventive process even without aluminum sulfate pretreatment. However, the concentration of fluorides in the steam distillate was higher than the initial overall concentration, since fluorides tend to concentrate in the initial steam distillate. Even when starting with relatively low-fluoride concentration material, it may be desirable to use the aluminum sulfate pretreatment option to minimize the fluoride content during the steam distillation.

EXAMPLE 3

A 1-liter solution containing 20 weight % of PFOA sodium salt (0.459 moles) was treated with 2 molar equivalents of concentrated sulfuric acid (89.9 g). The mixture was warmed to 50° C., and the phases were separated. The bottom organic layer weighed 231.2 g. This solution was distilled at atmospheric pressure, using a still-pot temperature of 102° C. to 106° C. and a head temperature of 102° C., collecting 18.3 g of a 15 weight % solution of PFOA in water. The system was then cooled and placed under vacuum and distilled, using 50° C. water on the condensor to prevent freezing and plugging. The yield was 160 g of PFOA. The still heel was 49.5 g. Yield of PFOA from the combined distillate fractions was 84%.

Comparative Example 1

A test was carried out using the previously known steam distillation process. An 860 g solution of 20 wt % PFOA ammonium salt was treated with 82.6 g of concentrated sulfuric acid. It was then steam distilled to remove the PFOA, adding water to the still-pot to replace the distillate removed as the steam distillation progressed. The maximum concentration of PFOA in the distillate was 16 wt %. A process of reverse osmosis would be required to bring the concentration up to the desired 20%. Even after 1200 ml of distillate had been recovered, there was still 0.25 wt % of PFOA in the new distillate, showing that the steam distillation process does not have a well-defined end-point. The total amount of distillate at this point was about 7 times the weight of PFOA recovered, showing the very poor energy efficiency of this process.

The inventive examples are superior to the above Comparative Example in terms of space-time efficiency, avoidance of re-concentrating the PFOA by reverse osmosis, and in energy consumption.

What is claimed is:

1. A process comprising (A) acidifying an aqueous solution comprising an alkali metal salt of a fluorinated alkanoic acid with an acid to produce an acidified solution, (B) heating said acidified solution to produce an organic layer, which comprises said fluorinated alkanoic acid, and an aqueous layer, (C) separating and recovering said organic layer from the aqueous layer, (D) washing said organic layer with an acid solution, (E) isolating said fluorinated alkanoic acid, and (F) optionally converting said fluorinated alkanoic acid to ammonium or alkali metal salt wherein said acid used in step (A) contains less than about 50 volume % water; said acid solution used in step (D) contains less than about 10 volume % acid; and the pH of said acidified solution is about 2 or less.

2. The process of claim 1 wherein said fluorinated alkanoic acid has the formula of X—$R_f$—COOH; X is hydrogen, fluorine, chlorine, or combinations thereof; $R_f$ is a fluorinated group having 5 to 12 carbon atoms per group; and said acidified aqueous solution has a pH of about 2 or less.

3. The process of claims 1 wherein said fluorinated alkanoic acid is perfluorinated.

4. The process of claim 1 wherein said fluorinated alkanoic acid is perfluorooctanoic acid.

5. The process of claim 1, 2, 3, or 4 wherein said aqueous solution is treated, prior to the step (A), with a soluble aluminum salt.

6. The process of claim 1, 2, 3, or 4 wherein said acidified aqueous solution produced in step (A) is treated, prior to step (B), with a soluble aluminum salt.

7. The process of claim 1, 2, 3, or 4 wherein the acid is sulfuric acid.

8. The process of claim 5 wherein the acid is sulfuric acid.

9. The process of claim 6 wherein the acid is sulfuric acid.

10. The process of claim 7 wherein said heating in step (B) is carried out at a temperature of about 35° C. to about 60° C.

11. The process of claim 8 wherein the soluble aluminum salt is aluminum sulfate.

12. The process of claim 9 wherein the soluble aluminum salt is aluminum sulfate.

13. The process of claim 11 wherein said heating in step (B) is carried out at a temperature of about 35° C. to about 60° C.

14. The process of claim 12 wherein said heating in step (B) is carried out at a temperature of about 35° C. to about 60° C.

15. The process of claim 1 wherein the alkali metal is sodium.

16. The process of claim 1 wherein the process is a batch process.

17. The process of claim 1 wherein the process is continuous.

* * * * *